US012805754B2

(12) United States Patent
Cathelain et al.

(10) Patent No.: US 12,805,754 B2
(45) Date of Patent: Nov. 24, 2026

(54) BALLISTOCARDIOGRAPHY DEVICE AND METHOD

(71) Applicants: PARIS SCIENCES ET LETTRES, Paris (FR); ÉCOLE PRATIQUE DES HAUTES ÉTUDES, Paris (FR)

(72) Inventors: Guillaume Cathelain, Paris (FR); François Jouen, Paris (FR); Rémy Jaffres, Paris (FR)

( * ) Notice: Subject to any disclaimer, the term of this patent is extended or adjusted under 35 U.S.C. 154(b) by 1109 days.

(21) Appl. No.: 17/593,848

(22) PCT Filed: Mar. 30, 2020

(86) PCT No.: PCT/EP2020/058996
§ 371 (c)(1),
(2) Date: Sep. 26, 2021

(87) PCT Pub. No.: WO2020/193812
PCT Pub. Date: Oct. 1, 2020

(65) Prior Publication Data

US 2022/0167875 A1 Jun. 2, 2022

(30) Foreign Application Priority Data

Mar. 28, 2019 (FR) ...................................... 1903297

(51) Int. Cl.
*A61B 5/11* (2006.01)
*A61B 5/00* (2006.01)
(Continued)

(52) U.S. Cl.
CPC ........ *A61B 5/1102* (2013.01); *A61B 5/02405* (2013.01); *A61B 5/0816* (2013.01);
(Continued)

(58) Field of Classification Search
CPC . A61B 5/1102; A61B 5/02405; A61B 5/0816; A61B 5/4818; A61B 5/6892;
(Continued)

(56) References Cited

U.S. PATENT DOCUMENTS

2010/0016685 A1 1/2010 Muehlsteff
2012/0123279 A1* 5/2012 Brueser ................ A61B 5/1102
600/481
(Continued)

FOREIGN PATENT DOCUMENTS

DE 202008018439 U1 11/2013
WO 9819596 A1 5/1998

OTHER PUBLICATIONS

ISR; European Patent Office; Netherlands, Jul. 2, 2020.

*Primary Examiner* — Abid A Mustansir
(74) *Attorney, Agent, or Firm* — Patshegen IP; Moshe Pinchas

(57) ABSTRACT

The ballistocardiography device (200) comprises:

a non-homogeneous and anisotropic support (105) having a portion forming a stress or deformation guide (205) and a portion transmitting fewer stresses or deformations in the frequency range between 0.05 Hz and 25 Hz, and at least one sensor (210) of a signal representing at least one movement and/or variation of quasi-static stress of the guide in the frequency range between 0.05 Hz and 25 Hz, positioned facing the stress or deformation guide.

The stress or deformation guide is on the surface.

16 Claims, 10 Drawing Sheets

(51) Int. Cl.
*A61B 5/024* (2006.01)
*A61B 5/08* (2006.01)

(52) U.S. Cl.
CPC .......... *A61B 5/4818* (2013.01); *A61B 5/6892* (2013.01); *A61B 5/7225* (2013.01); *A61B 5/7275* (2013.01); *A61B 2560/0223* (2013.01); *A61B 2562/0247* (2013.01)

(58) Field of Classification Search
CPC ................ A61B 5/7225; A61B 5/7275; A61B 2560/0223; A61B 2562/0247
See application file for complete search history.

(56) References Cited

U.S. PATENT DOCUMENTS

| | | | | |
|---|---|---|---|---|
| 2014/0371635 | A1 | 12/2014 | Shinar et al. | |
| 2015/0141852 | A1* | 5/2015 | Dusanter ............. | A61B 5/0022<br>600/484 |
| 2015/0351693 | A1 | 12/2015 | Berezhnyy et al. | |

* cited by examiner

1000

1100

BALLISTOCARDIOGRAPHY DEVICE AND METHOD

TECHNICAL FIELD OF THE INVENTION

The present invention relates to a ballistocardiography device and method. It applies, in particular, to ballistocardiography, i.e., to the non-invasive measurement of mechanical cardiac activity.

STATE OF THE ART

The support materials and textiles used for ballistocardiography are elastic and/or viscous for the individual's comfort, and deform isotropically when subjected to a mechanical load. The deformation or pressure is measured, for the individual's comfort, remotely from the load area, i.e. from the surface of contact between the individual and his mechanical support. The mechanical support, for example a mattress, is deformed during the passage of blood in an artery: either in the direction normal to this surface, or in the direction tangential to this surface.

This distance between the load area and the measurement point produces a low deformation/pressure energy density, and consequently the amplitude and signal-to-noise ratio of the ballistocardiogram are low. In effect, a cone effect, which depends on the elasticity and viscosity of the mechanical support, is produced: the deformation/pressure energy density decreases as the distance between the measurement point and the contact area increases.

This diffusion phenomenon is chiefly produced on foams and textiles. With the aim of measuring a ballistocardiogram with an amplitude and signal-to-noise ratio sufficient to detect cardiac activity, the designers and manufacturers use very sensitive sensors, steps of analog filtering, and very high resolution analog/digital converters, with the drawback of high cost and a signal-to-noise ratio that is not sufficient for digital signal processing.

In addition, unlike other cardiac measurement devices such as electrocardiograms or pulse oximeters, no measurement protocol is properly established since the deformation and pressure densities measured vary greatly according to the mechanical environment of the individual. For an application in the field of smart bedding, each ballistocardiogram would therefore have to be specified by the bedding technology, the technology of the sensor(s) and the position of the sensor(s) on or in the bedding, which would make the use of this device—especially in clinical settings where the measurements must be repeatable in an identical way—not applicable.

Ballistocardiograms are currently measured by several sensor technologies: pressure sensors or movement sensors.

These sensors can be incorporated into a bed. They measure ballistocardiograms that are not repeatable, because the amplitudes vary according to the mechanical environment of the individual. In addition, the signal-to-noise ratio is sometimes insufficient despite a high-performance acquisition chain.

FIG. 1 represents, schematically, the existing devices. A user 130 (seen in cross-section) is lying on a mattress 105. The mattress 105 is positioned on a bed base equipped with a stress sensor 110 and/or the mattress comprises an inclination or movement sensor 115. The sensors capture a deformation or inclination linked to quasi-static movements 120 caused by the breathing and heartbeats of the user 130.

SUBJECT OF THE INVENTION

The present invention aims to remedy all or part of these drawbacks.

To this end, according to a first aspect, this invention envisages a ballistocardiography device, which comprises:

- a non-homogeneous anisotropic support having a portion forming a stress or deformation guide and a portion transmitting fewer stresses or deformations in the frequency range between 0.05 Hz and 25 Hz; and
- at least one sensor of a signal representing at least one movement and/or variation of quasi-static stress of the guide in the frequency range between 0.05 Hz and 25 Hz, positioned facing the stress or deformation guide, wherein the stress or deformation guide is on the surface.

Thanks to these provisions, the measurement of a ballistocardiogram is obtained in high resolution and in a repeatable way, regardless of the nature of the mechanical support of the individual and without causing discomfort to him. The elasticity and viscosity of the support material are reduced, and the diffusion of deformation/compression energies by cone effect in the direction of the sensor is also reduced.

It is also possible to place the sensor on one side of the support, far from the thorax, or on the surface on which a user rests. For example, the sensor can be placed in a corner or at the user's feet, far from the thorax, so the user is not inconvenienced.

Moreover, the device costs less than the known solutions, since the technical specifications of the sensor can be lower without affecting the ballistocardiogram obtained.

In some embodiments:

- the stress or deformation guide covers the support at least partially;
- the stress or deformation guide is tensioned along its length;
- the device comprises a means for tightening under tension the stress or deformation guide around the support;
- the device comprises a means for fastening to a rigid portion of the support;
- the tightening or fastening means does not cover the entire width of the stress or deformation guide; and/or
- the device comprises a receptacle for a portable communicating terminal, such as a smartphone or a digital tablet.

In some embodiments, the stress or deformation guide has a Young's modulus at least 10% higher than the value of the Young's modulus outside the stress or deformation guide in at least one direction.

These embodiments enable the stress or deformation to be transmitted effectively.

In some embodiments, the support has a generally parallelepipedal shape, whose largest dimension is called the "length", smallest dimension is called the "thickness", and intermediate dimension is called the "width".

These embodiments make it possible to utilize the device while the user is resting, for example while the user is sleeping.

In some embodiments, at least one sensor is a sensor for capturing an inclination of the guide, and the stress or deformation guide is positioned in a direction parallel to the width and passing through a source of stresses or deformations.

The advantage of these embodiments is to position the sensor on the surface of the stress or deformation guide, and therefore to replace or remove it more easily.

In some embodiments, at least one sensor is a pressure sensor, and the guide is positioned in the thickness of the support under a source of stresses or deformations.

These embodiments make it possible to avoid having the sensor visible or possibly damaged in regard to a position on the support.

In some embodiments, the stress or deformation guide has a Young's modulus with a progressive value.

The advantage of these embodiments is to make the user's contact on the stress or deformation guide more comfortable.

In some embodiments, the stress or deformation guide comprises at least one woven material.

Thanks to these provisions, the stress or deformation guide can be incorporated visually or mechanically into bedding or rest materials.

In some embodiments, the device that is the subject of the invention also comprises a means for processing each signal captured by each sensor, and a means for comparing to at least one predefined model in order to deduce trends, troubles or anomalies from this.

These embodiments make it possible to process the data from each sensor.

According to a second aspect, the present invention envisages a ballistocardiography method, utilizing a device that is the subject of the invention, which comprises the following steps:

- capturing a signal representative of at least one movement and/or variation of quasi-static stress produced by a user and traversing a support;
- segmenting the captured signal;
- filtering at least one segment of the captured signal providing a signal representative of a cardiac activity comprising at least two heartbeats;
- applying a model to each period of the signal representative of a cardiac activity; and
- determining a heart rate and/or heart rate variability.

As the particular aims, advantages and features of the method that is the subject of the invention are similar to those of the device that is the subject of the invention, they are not repeated here.

The signal can also be analyzed more precisely because the results are physiologically consistent.

In addition, the device whose data are processed by means of the method that is the subject of the invention, can be incorporated directly in a mattress or bedding because the sensor can be of lower quality and therefore less costly. In particular, the noise density of the acceleration can be higher. Thus, the device that is the subject of the invention is suitable for installation in clinical settings, without requiring dedicated staff.

In some embodiments, the method that is the subject of the invention comprises a phase of calibrating the model, which comprises the following steps:

- capturing a signal representative of a movement and/or variation of quasi-static stress produced by a user and traversing a support;
- segmenting the captured signal;
- detecting an envelope and at least one period for each signal segment;
- calculating a center of each envelope in the period;
- superimposing centers of each period; and
- for each segment of the signal, creating a cardiac model corresponding to the mean of the superimposed points at each instant of the predefined period.

These embodiments make it possible to calibrate the analysis of the signals from each sensor of the device as a function of the user and the support.

In some embodiments, the filtering step supplies a signal representative of a respiratory activity, the method also comprising a step of determining a respiratory frequency and/or apnea/dyspnea events as a function of at least one signal segment representative of a respiratory activity.

Thanks to these provisions, cardiac and respiratory information is obtained from the analysis of the same signal.

In some embodiments, the segmentation step comprises a step of removing each signal segment representative of a movement by the user and/or an absence of the user on the support.

These embodiments make it possible to study only the periods during which the user is at rest on the support.

BRIEF DESCRIPTION OF THE FIGURES

Other advantages, aims and particular features of the invention will become apparent from the non-limiting description that follows of at least one particular embodiment of the device and method that are the subjects of the invention, with reference to drawings included in an appendix, wherein.

DESCRIPTION OF EMBODIMENTS

The present description is given in a non-limiting way, in which each characteristic of an embodiment can be combined with any other characteristic of any other embodiment in an advantageous way.

Note that the figures are not to scale.

The following definitions are noted here:

a direction in geometry is an equivalence class defined in a set of straight lines or planes by the parallel relationship;

a non-homogeneous environment is an environment whose properties are not the same at all points of the environment;

an anisotropic environment is an environment whose properties are dependent on the direction;

the Young's modulus, or (longitudinal) elasticity modulus or tensile modulus, is the constant that links the tensile (or compressive) stress and the beginning of the deformation of an isotropic elastic material; and the rigidity tensor generalizes the Young's modulus to anisotropic materials.

In the rest of the text, "Young's modulus" refers to both the rigidity tensor of an anisotropic material and the Young's modulus of an isotropic material.

Figure 1:
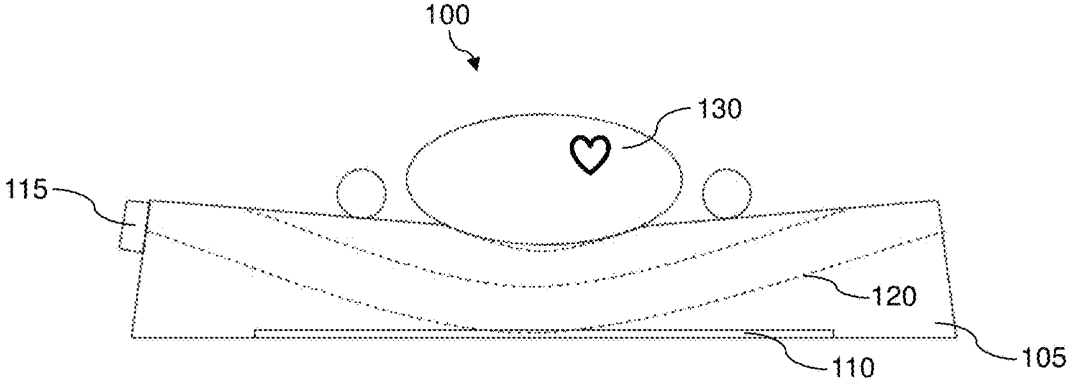
FIG. 1 represents, schematically, the prior state of the art of the invention.
Figure 2:
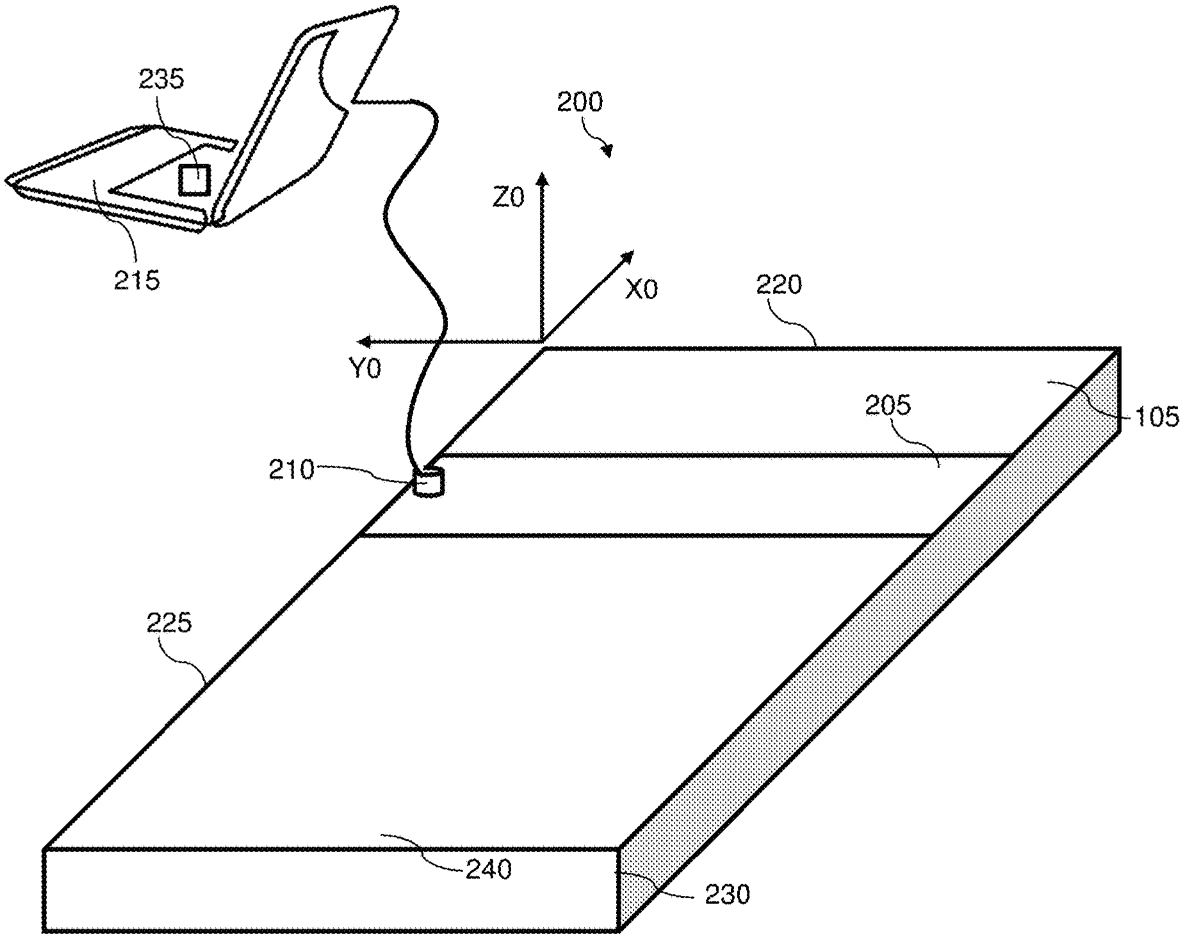
FIG. 2 represents, schematically, a first embodiment of the device that is the subject of the invention.

FIG. 2, which is not to scale, shows a schematic view of a first embodiment of a device that is the subject of the invention.

The ballistocardiography device 200 comprises:

a non-homogeneous anisotropic support 105 having a portion forming a stress or deformation guide 205 and a portion 240 transmitting fewer stresses or deformations in the frequency range between 0.05 Hz and 25 Hz; and at least one sensor 210 providing a signal representative of at least one movement and/or variation of quasi-static stress of the guide 205 in the frequency range between 0.05 Hz and 25 Hz, positioned facing the guide 205.

The frequencies 0.05 Hz to 25 Hz contain the cardiac and respiratory phenomena.

Preferably, the stress or deformation guide 205 has a Young's modulus at least 10% higher than the value of the Young's modulus outside the guide 205 in at least one direction.

Figure 3:
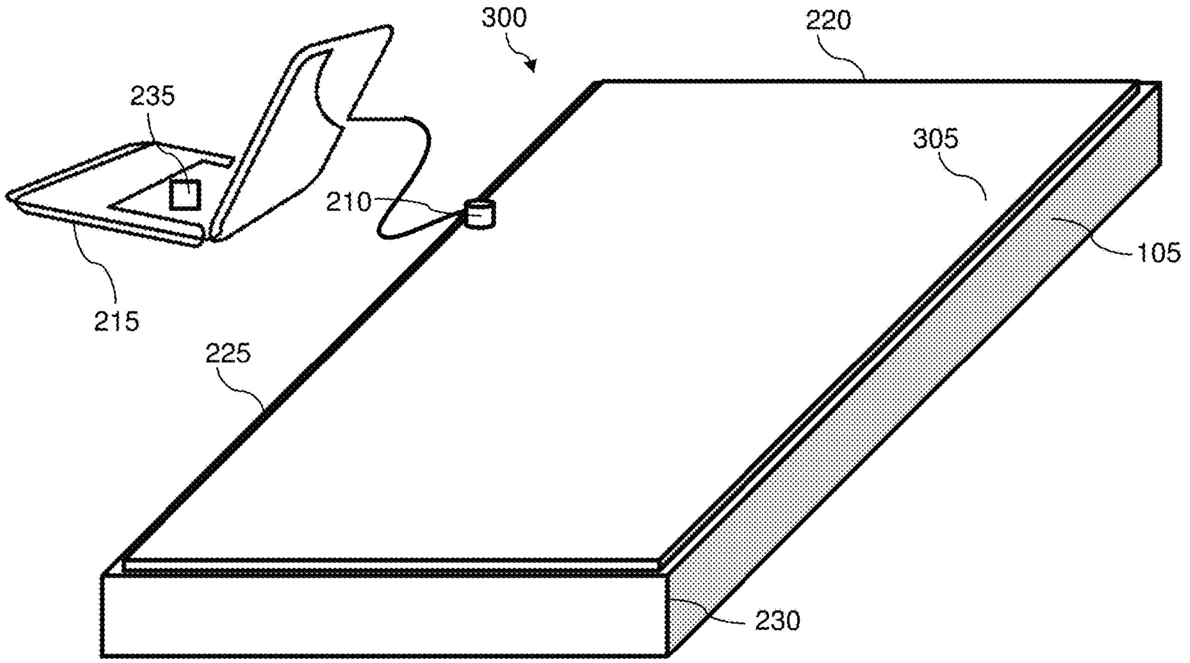
FIG. 3 represents, schematically, a second embodiment of the device that is the subject of the invention.
Figure 4:
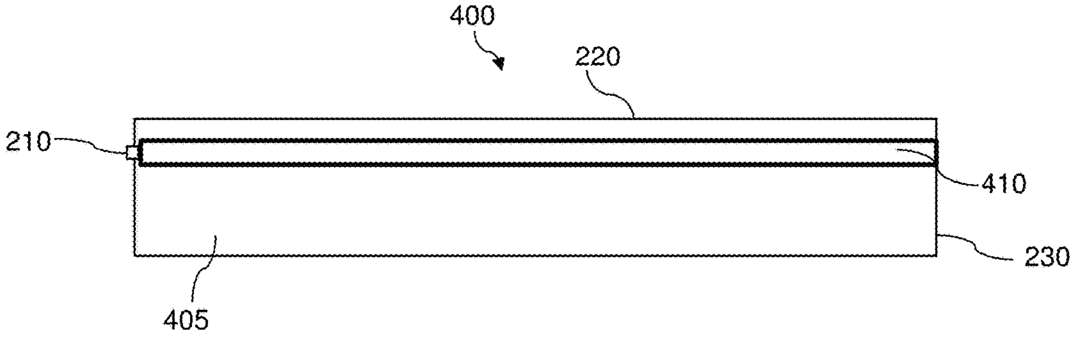
FIG. 4 represents, schematically, a third embodiment of the device that is the subject of the invention.

In FIGS. 2, 3 and 4, the guides 205, 305 and 410 are deformation guides. It is more pertinent to measure a movement for FIGS. 2, 3 and 4 when the exterior surface of the sensor is loose (the stress is therefore almost zero) and to measure a stress when the guide is under tension, the movement therefore being almost zero.

The support 105 is, for example, a mattress made of a material known to the person skilled in the art. Preferably, the support 105 has a generally parallelepipedal shape, whose largest dimension 225 is called the "length", smallest dimension 230 is called the "thickness", and intermediate dimension 220 is called the "width".

In the embodiments shown in FIGS. 2 and 3, the surfacic deformation guide, 205 or 305, is positioned on the support 105. In the embodiment shown in FIG. 4, the surfacic deformation guide 410 is positioned inside the support.

In the embodiment shown in FIG. 2, the deformation guide 205 is on the surface and partially covers the support 105. The portion of the support 105 covered by the deformation guide 205 corresponds to the portion of the support 105 on which a user's thorax is positioned while the device 200 is used.

A surfacic element is defined as an element in which one dimension is negligible in relation to the other dimensions. In other terms, an element is surfacic if one dimension is at least ten times, preferably thirty times, and even more preferably one hundred times, less than two other dimensions of an orthonormal reference space.

Preferably, the deformation guide 205 is positioned in a direction parallel to the width and passing through a source of deformation. The deformation source is the user's thorax, with movements affected by the user's breathing and by the user's heartbeats.

Figure 17:
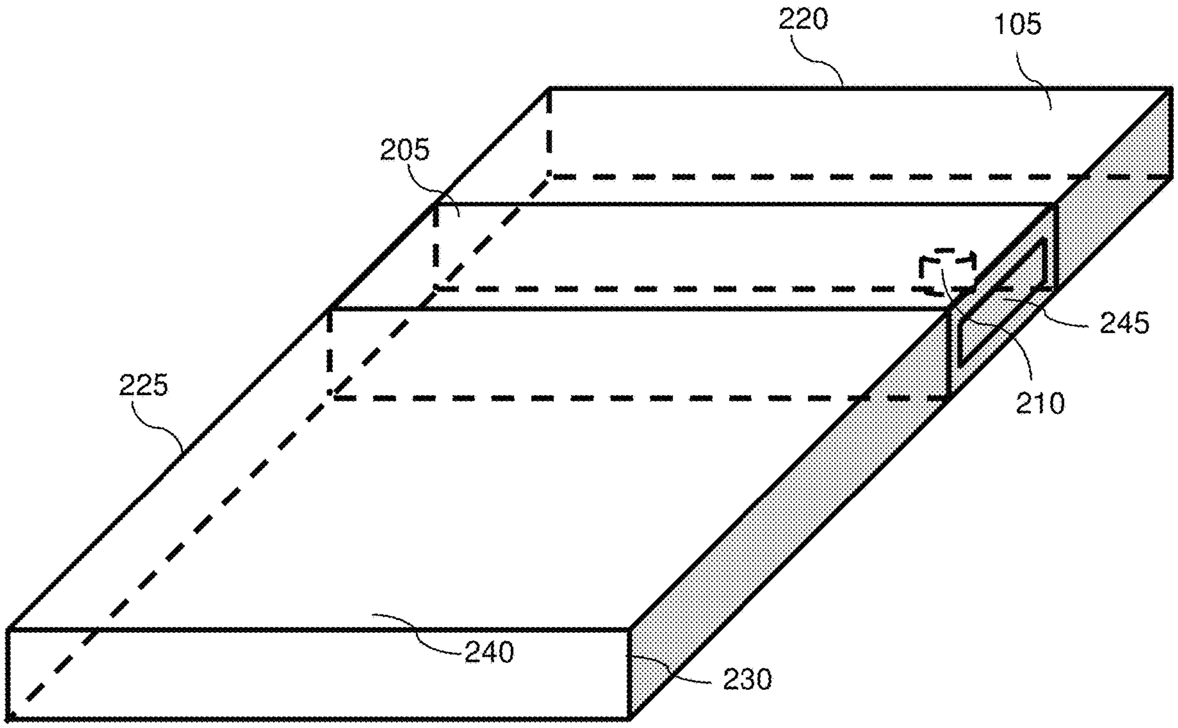
FIG. 17 represents, schematically, a first variant of the embodiment shown in FIG. 2.

The deformation guide 205 is preferably free to move relative to the support 105 to have a lower coefficient of friction between the deformation guide 205 and the support 105. In some embodiments, the deformation guide 205 and/or the support 105 include a self-adhesive, stitched or glued fastening means. In the first variant of the embodiment shown in FIG. 2 represented in FIG. 17, the deformation guide 205 goes round the mattress across its width. A fastening means 245 fastens two ends of this guide 205. In some variants, the guide 205 takes the form of a continuous strip, each segment of which serves as a fastening means. FIG. 17 also shows that the sensor 210 is between the guide 25 and the mattress 105.

Figure 18:
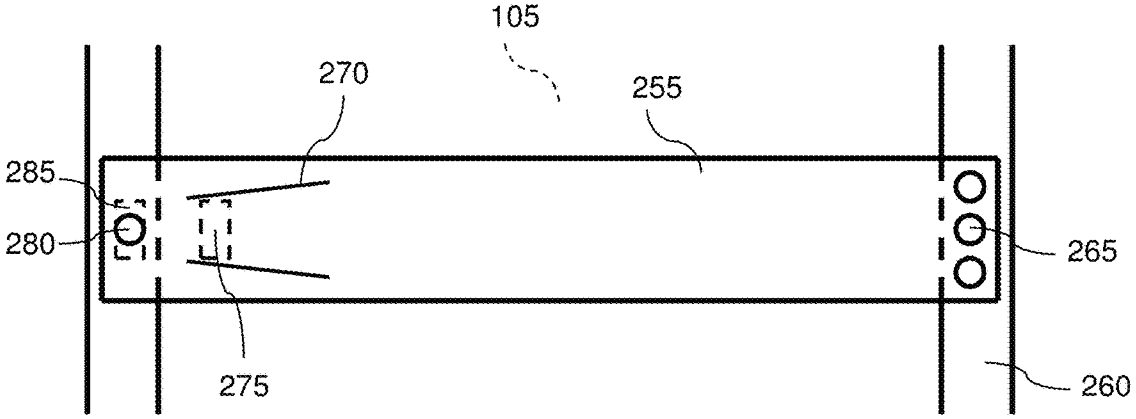
FIG. 18 represents, in a partial top view, a second variant of the embodiment shown in FIG. 2.

In the second variant of the embodiment shown in FIG. 2 represented in FIG. 18 in a partial top view, the guide 255 is held taut between rigid portions 260 of the bed, for example the frame of the bed base or bedpost, by fastening means, 265 on one side and 280 on the other side. Preferably, the fastening means closest to the sensor 275 or 285, here the fastening means 280, is limited, i.e. covers a small portion of the width (defined as for the support 105) of the guide 255, so that the stresses and deformations are focused on this sensor. Note that folds 270 can be formed on the guide 255. Two sensor positions (dedicated sensor or smartphone) are shown in FIG. 18: in position 275 between the guide 255 and the support 105, and in position 285 on the rigid portion 260. In the two variants shown in FIGS. 17 and 18, the guide 205 and 255 is taut, which promotes the propagation of deformations and stresses along this guide, i.e. from the user's thorax, the source of these deformations and stresses, to the sensor 210, 275 or 280.

In the same way, in the variant shown in FIG. 17, preferably the fastening means 245 is limited and does not cover the entire width of the guide 205 for focusing the stresses and deformations on the sensor 210 positioned near this fastening means 245.

Thus, the deformation guide 205 can comprise a tightening means, for example a tightening loop connected to each end of the deformation guide to surround the support 105. Preferably, the surface guide 205 is tensioned along its length, for example by tightening the tightening means or fastening under tension the fastening means.

In some embodiments, the deformation guide has the form of a belt, preferably stretched around the support 105 along the width and thickness at the place where the user positions his thorax when he uses the device 200. The belt can be made of a polymer or cotton twill.

Serge is a fabric produced with one of the three main weave patterns known as twill. Thus, serge refers to all of the textiles produced by this type of weave, which is characterized by diagonal ribs on the face and back of the fabric. It can have a warp or weft effect. This is known as a step weave.

The deformation guide can be a material that is homogeneous or not, anisotropic or not. In some embodiments, the deformation guide is a woven material. The woven material can be a three-dimensional fabric known to the person skilled in the art.

In some embodiments, the deformation guide 205 has a Young's modulus with a progressive value. For example, when the deformation guide is made of fabric, the tension of the fabric increases as one gets further away from the source of stresses and deformations. In another example, the deformation guide is an assembly of rectangular pieces of fabric, those close to the source being more elastic than those close to the sensor 210.

In the embodiment shown in FIG. 2, the sensor 210 is an inclination or movement sensor, for example an inclinometer, or more generally based on an accelerometer or a gyroscope.

Preferably, the sensor 210 is positioned under the guide 205 and/or distant from the user's sleeping area, to avoid inconveniencing him. In some embodiments, the sensor 210 is attached removably to the guide 205, for example by means of a self-adhesive fabric, an adhesive, a seam or a magnetic mount.

The device 200 also comprises a means 215 for processing each signal captured by each sensor 210, and a comparison means 235 comprising at least one predefined model in order to deduce trends, troubles or anomalies from this. In some embodiments, the device 200 comprises a signal acquisition board configured to package, filter and amplify the analog measurement from the sensor 210.

In some embodiments, the acceleration noise density of the sensor is less than 14 μg/sqrt(Hz), where "sqrt" means the square root. More preferably, the acceleration noise density is less than 90 μg/sqrt(Hz).

One advantage of accelerometer type deformation sensors 210 compared to stress sensors is the ability to measure the ballistocardiogram along several axes, unlike the single-direction stress sensors generally used in ballistocardiography.

Preferably, the processing means 215 and the comparison means 235 are incorporated into a communicating terminal, and/or into an application server, which executes a processing and comparison computer program. Preferably, the computer program comprises the steps of the method that is the subject of the invention.

One defines, with regard to FIGS. 3 and 4, the geometric characteristics differentiating the embodiments shown from the embodiment shown in FIG. 2.

In the embodiment shown in FIG. 3, the deformation guide 305 is on the surface and covers the support 105 on one surface of the support comprising two orthogonal axes, one in the direction of the width, the other in the direction of the length. The deformation guide 305 can be positioned on the support 105 like a fitted sheet or a mattress cover. In some embodiments, the deformation guide 305 is made of cotton twill.

In the embodiment shown in FIG. 4, the deformation guide 410 corresponds to the embodiments described with regard to FIGS. 2 and 3 and placed in the support 405. The deformation guide 410 is preferably located at least in the area under which the user's thorax is positioned when the device 400 is used. In some embodiments, the deformation guide 410 is volumetric, i.e. no dimension is negligible. Preferably, the deformation guide 410 is made of a three-dimensional textile known to the person skilled in the art.

In the embodiment shown in FIG. 4, the sensor 210 is positioned on one surface of the support 405 having one direction parallel to the thickness and one direction parallel to the length. In some embodiments, the sensor 210 is integrated into the support 405, i.e. the sensor is incorporated into the volume defined by the support 405.

In some embodiments, a predetermined weave pattern is defined that makes it possible to reinforce the transmission of the stress or deformation in the guide.

In some embodiments, the guide is made of a three-dimensional textile with elasticity properties that differ in the direction of the width according to the latitude. The term "latitude" refers to a coordinate of a point on the support in the direction of the width.

In some embodiments, the guide is made of woven material and comprises an assembly of at least two woven materials.

In some embodiments, the sensor is miniaturized so as to measure very localized deformations and be able to be attached to textile fibers.

In some embodiments, several sensors are positioned within or on the same support to merge data, better separate the mechanical sources in the signal and increase the signal-to-noise ratio.

In some embodiments, at least one sensor is a communicating and/or autonomous sensor.

In some embodiments, at least one sensor and the processing means are incorporated into a single housing.

In some embodiments, the device that is the subject of the invention comprises a receptacle for a portable communicating terminal, such as a smartphone or digital tablet, comprising a lower quality accelerometer for amplifying the ballistocardiogram. That means that a sensor of the device that is the subject of the invention is incorporated into a portable communicating terminal. These embodiments enable a ballistocardiogram to be measured directly on a portable communicating terminal. Currently the sole technology for analyzing sleep by smartphone only uses actigraphy, which is much less effective than ballistocardiography. In actigraphy access to heart rate variability data, which enables good classification of sleep cycles, is not possible.

In some embodiments, the processing means comprises an analog-digital acquisition means that utilizes the following functions, in order:

application of a high-pass analog filter;

amplification;

application of an anti-aliasing filter;

an analog-digital conversion.

For example:

the high-pass analog filter is a first-order filter with a cutoff frequency of 0.05 Hz;

the amplifier has a gain multiplier of 500;

the anti-aliasing filter is a first-order low-pass analog filter with a cutoff frequency equal to half the sampling frequency; and the converter encodes the digital signal over at least twelve bits with a frequency of at least 200 Hz.

In some embodiments, the coefficient of friction between the support and the deformation guide is minimized. For the deformation guide, a movement sensor placed at the end of the guide is used. As the friction coefficient gets higher, adhesion increases and the deformation guide has less freedom to deform.

Preferably, the sensor 210 comprises a means for communicating with the processing means 215. The communication means is, for example, a wireless communication means using the Bluetooth (registered trademark) or Zigbee (registered trademark) protocol. In some embodiments, the sensor comprises a rechargeable accumulator and a means for optimizing the energy chain.

Figure 5:
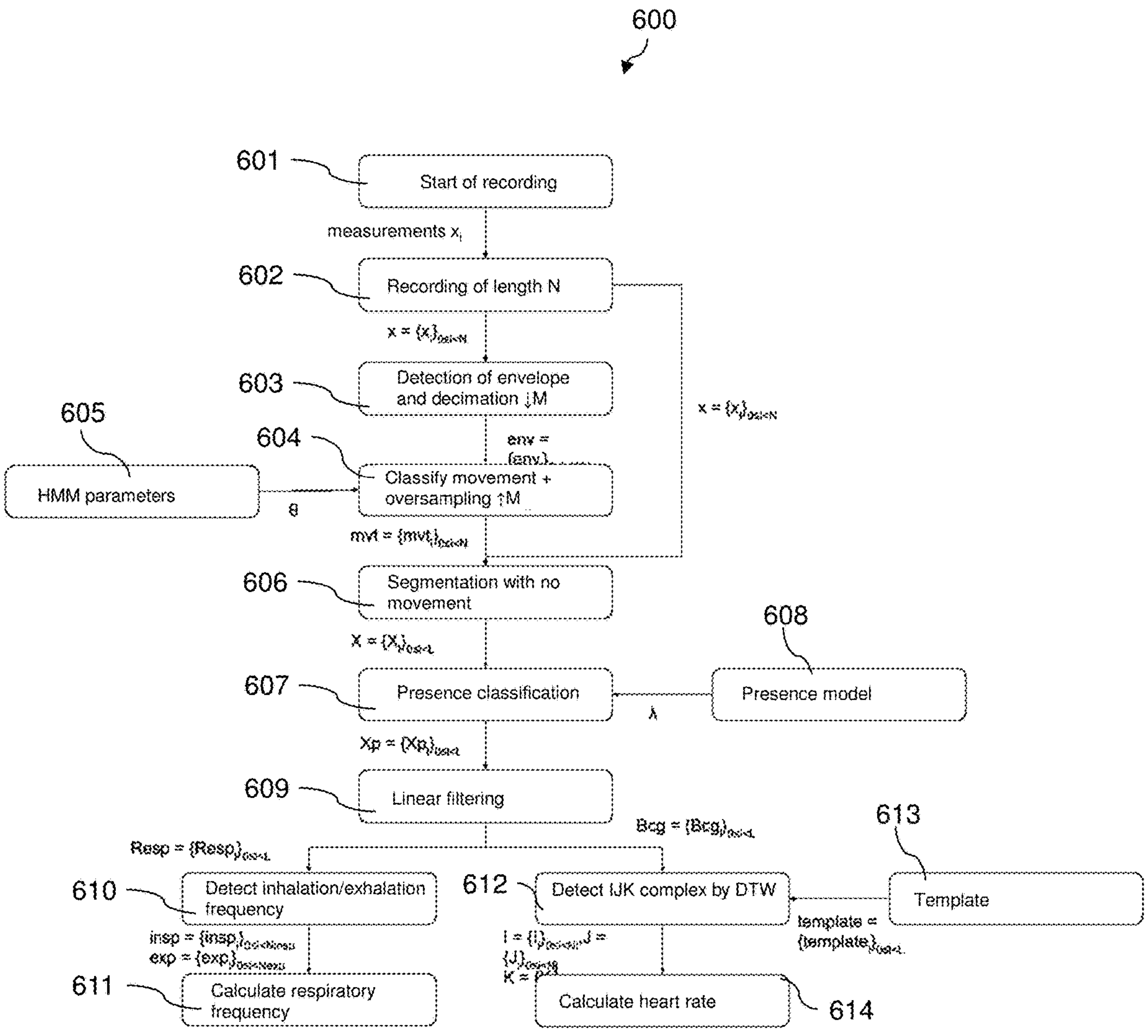
FIG. 5 represents, schematically and in the form of a logical diagram, a first particular series of steps of the method that is the subject of the invention.
Figure 6:
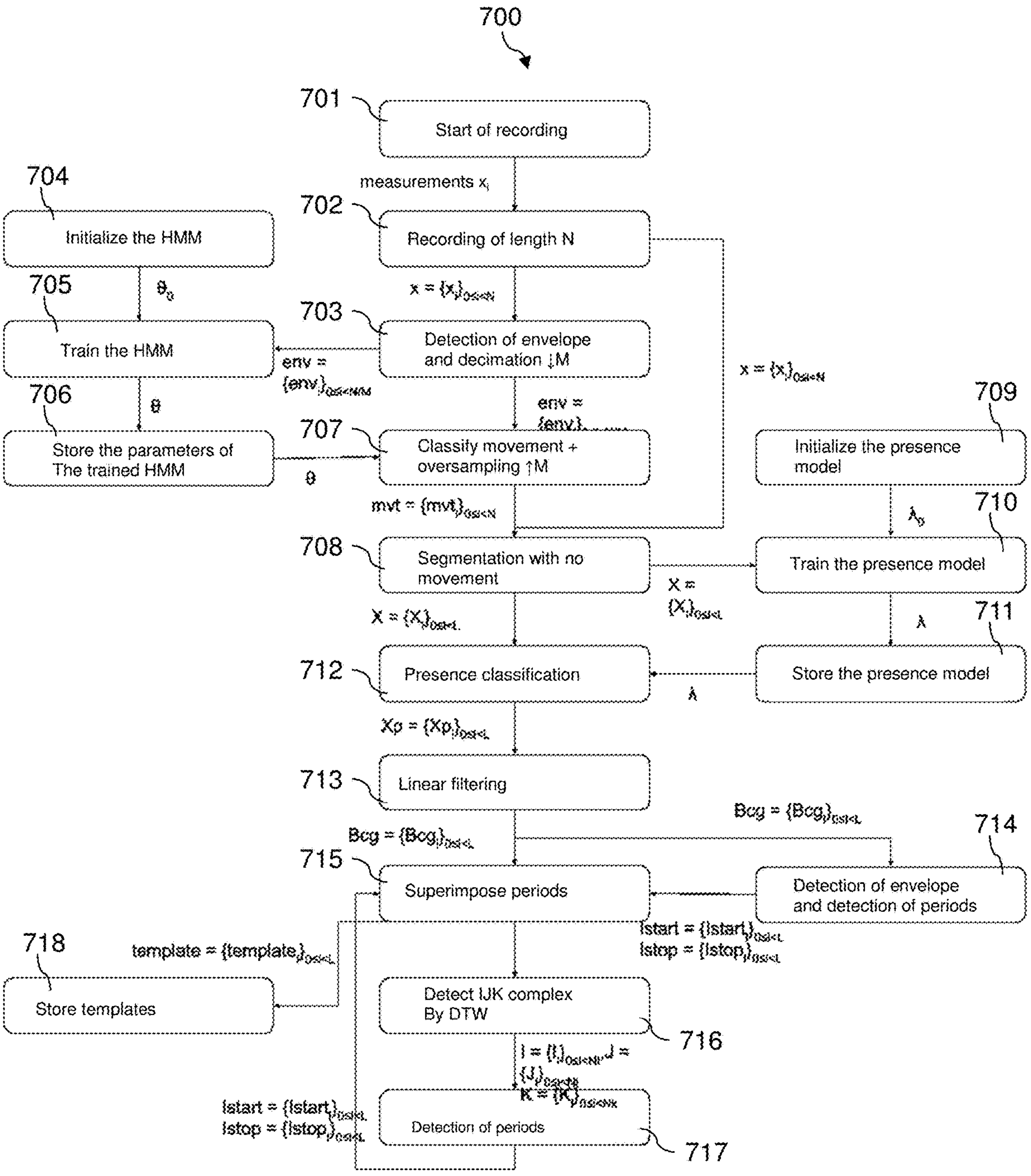
FIG. 6 represents, schematically and in the form of a logical diagram, a second particular series of steps of the method that is the subject of the invention.

FIG. 5 shows an embodiment of a ballistocardiography method 600 that is the subject of the invention.

The method 600 comprises the following steps:

capturing 601 a signal representative of a movement and/or variation of quasi-static stress produced by a user and traversing a support over a first predefined period;

segmenting, 603 to 608, the captured signal;

filtering 609 at least one segment of the captured signal providing a signal representative of a cardiac activity comprising at least two heartbeats;

applying 612 a model to each period of the signal representative of a cardiac activity; and determining 614 a heart rate and/or a heart rate variability.

The capture step 601 is preferably performed by means of a device 200, 300 or 400, that are the subjects of the invention. During the capture step 601, the signal corresponds to:

an inclination or movement whose variations are representative of the breathing and cardiac movements of a user on a support; or a stress whose variations are representative of the breathing and cardiac movements of a user on a support.

The method 600 can be utilized on signals from several sensors whose results are compared.

The signal, with a length of N samples, is recorded 602 and segmented. For example, a timestamp is added to each sample, i.e. this sample's measurement time is entered. In some embodiments, the recording step 602 is performed continuously and preferably in real time. For example, a microcontroller is placed in the same housing as the sensor and utilizes the method 600. The segmentation can also be called windowing. A segment, or a window, consists of several samples and can last between one second and ten minutes, for example. Preferably, the sampling frequency 602 is fixed and comprises between 200 Hz and 1 kHz.

The envelope is detected 603 for each segment and decimated. For example, the envelope can be detected 603 by applying a Hilbert transform to each segment, determining an absolute value of the signal or the Root Mean Square (acronym RMS) value of the signal. Decimation consists of keeping only one sample out of M, where M is the decimation rate. Preferably, M is between 20 and 1000.

Preferably, the segmentation steps 603 to 608 comprise a step, 604 to 607, of removing each signal segment representative of a movement by the user and/or an absence of the user on the support.

During a step 604, a Hidden Markov Model (acronym HMM) is applied. The hidden Markov model, whose parameters are defined in step 605, has two states: one state in which the observations correspond to movements, and one state in which the observations correspond to an absence of movement. In addition, during the step 604 an observation sequence corresponding to the envelope of the signal 603 is produced.

An observation is defined as a value of a signal at a given time: here it is the decimated envelope 603 that the accelerometer measures. An observation sequence is defined as a series of observations ordered in time.

In the model defined in step 604, it is assumed that the observation sequence is a random variable. The sequence of states is synchronized with the observation sequence. The sequence of states is deduced from the hidden Markov model thanks to the observation sequence using the Viterbi algorithm.

A Viterbi algorithm, based on the hidden Markov model, is applied to the observation sequence to find the sequence of states hidden behind the observation sequence, thus the signal can be classified 604 as observation subsequences, some sequences corresponding to movement and some sequences corresponding to the absence of movement.

Figure 7:
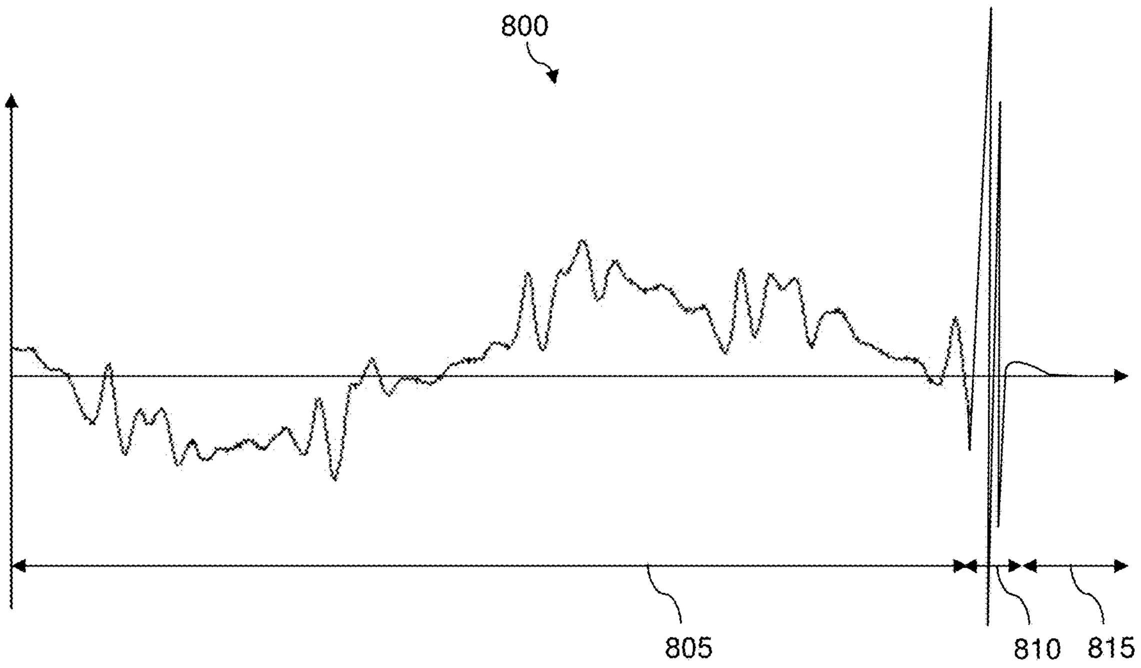
FIG. 7 represents, schematically, a signal obtained by a sensor of a device that is the subject of the invention.

The movement is shown in FIG. 7 by a signal 810 of large amplitude relative to the other magnitudes of the signal. In effect, when a user stirs on the support, the movements he makes cause a deformation and/or a stress whose order of magnitude is at least five times greater than the order of magnitude of the movements and/or stresses applied during heartbeats and breaths.

Preferably, an oversampling is performed during the classification step 604. The signal recorded in 602 is a sampling between 200 and 1000 Hz. The complexity of the Viterbi classification algorithm increases with the number of samples. For improved performance of the method 600, it is preferable to decimate the signal 603 before performing the classification to obtain an intermediate sampling frequency of 1 to 10 Hz, for example 4 Hz. After the classification, the signal is oversampled, by linear interpolation, for example with the same factor as the decimation factor. In this way, the performance levels of the classification algorithm are improved while retaining the same sampling frequency before and after the classification.

Once the classification has been performed, only the signals, 805 and 815, that are classified as not representing a movement by the user on the support are selected during a segmentation step 606.

Then, a presence model 608 is applied to the segmented signals during a step 607 of classifying a signal as a function of the presence of a user on the support. In effect when a user is absent from the support, the signal representative of this absence 815 has an amplitude of the order of the magnitude of noise.

The presence model is obtained by the calibration method 700. The presence model is formed of two Gaussian probability densities, A and B, each characterized by a standard deviation and a mean value. Density A has a high mean value and standard deviation: it corresponds to the presence of a user on the support with no movement. Density B has a low mean value and standard deviation: it corresponds to the absence of a user on the support.

For each signal segment with no movement 606, the mean value and standard deviation of the envelope of the signal are calculated: this is equivalent to considering a probability density Ci for each segment 606. This density Ci is associated to the closest of density A or density B, the closeness of the densities being defined here as a linear combination of the Euclidean distance between their mean value and the Euclidean distance between the standard deviations. In this way each segment with no movement 606 is classified according to the category "presence of the user on the support segment" or "absence of the user segment".

Only the segments classified as representative of the presence of a user on the support are used in the rest of the method 600.

A filtering step is applied to these segments 609. A band-pass filter, comprising a second-order infinite impulse response low-pass filter, with a cutoff frequency of 25 Hz and a quality factor of 0.707, and a second-order infinite impulse response high-pass filter, with a cutoff frequency of 5 Hz and a quality factor of 0.707, is applied to obtain a signal representative of a cardiac activity.

Figure 8:
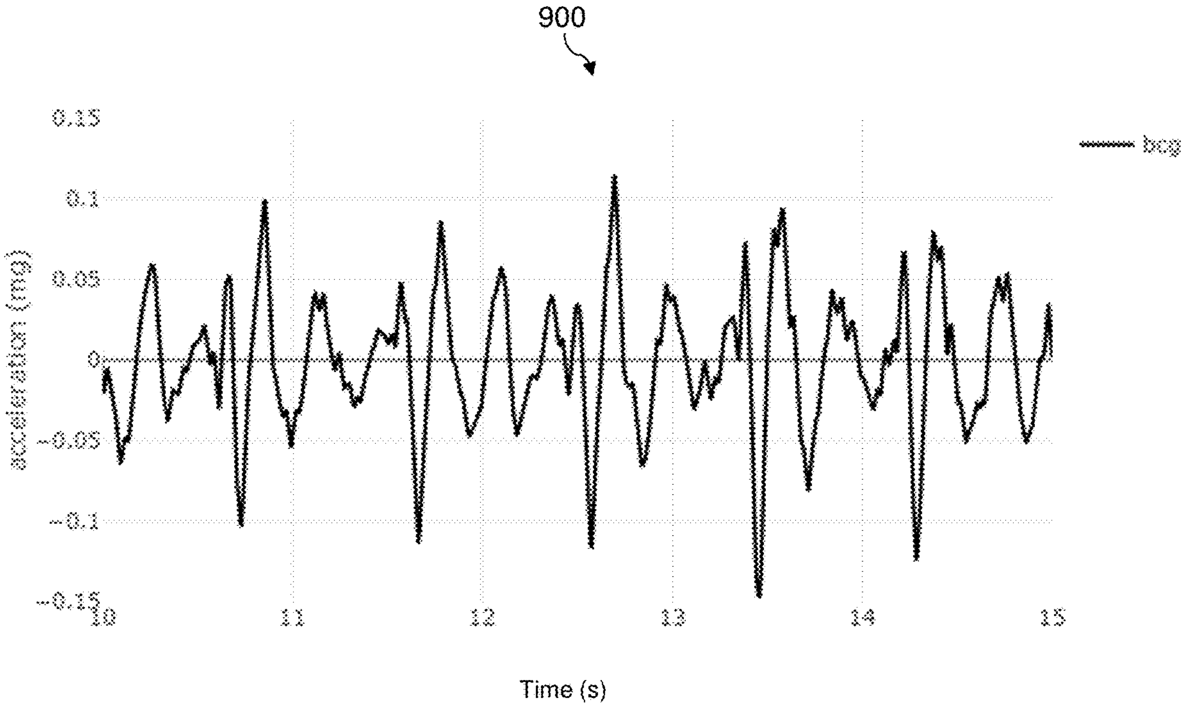
FIG. 8 represents, schematically, a signal after a filtering step of a method that is the subject of the invention.

The signal representative of a cardiac activity is shown in FIG. 8.

In some preferred embodiments, the filtering step 609 supplies a signal representative of a respiratory activity, the method also comprising a step, 610 and 611, of determining a respiratory frequency and/or apnea/dyspnea events as a function of at least one signal segment representative of a respiratory activity. A second-order infinite impulse response low-pass filter, with a cutoff frequency of 5 Hz and a quality factor of 0.707, is applied to obtain a signal representative of a respiratory activity.

Figure 12:
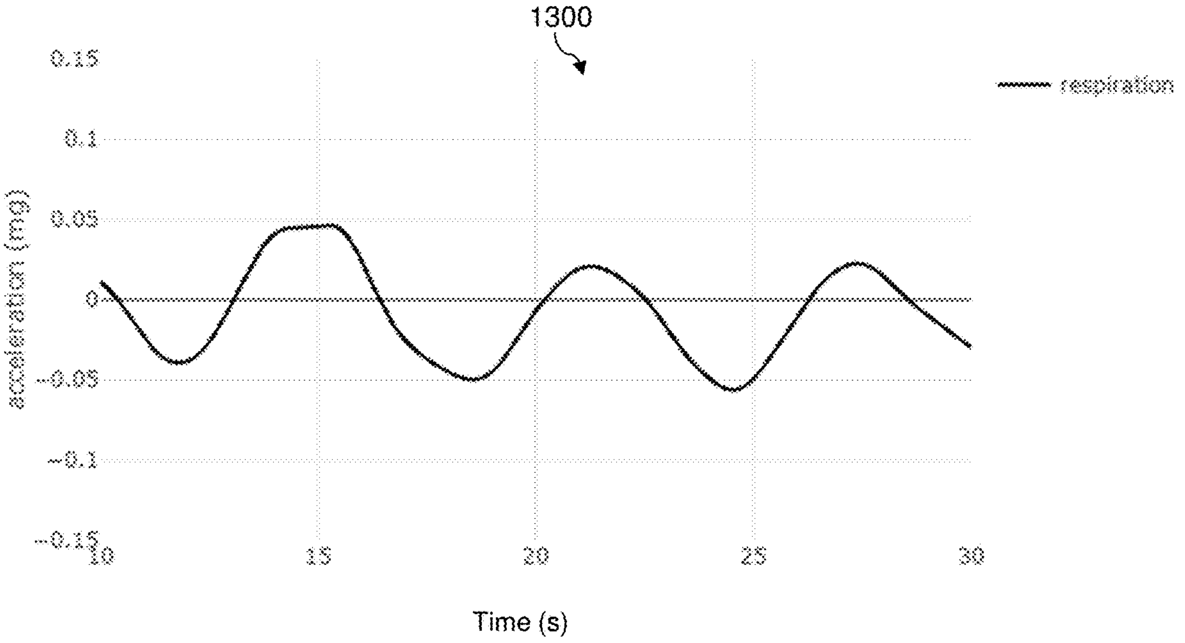
FIG. 12 represents, schematically, a signal after a filtering step of a method that is the subject of the invention.
Figure 13:
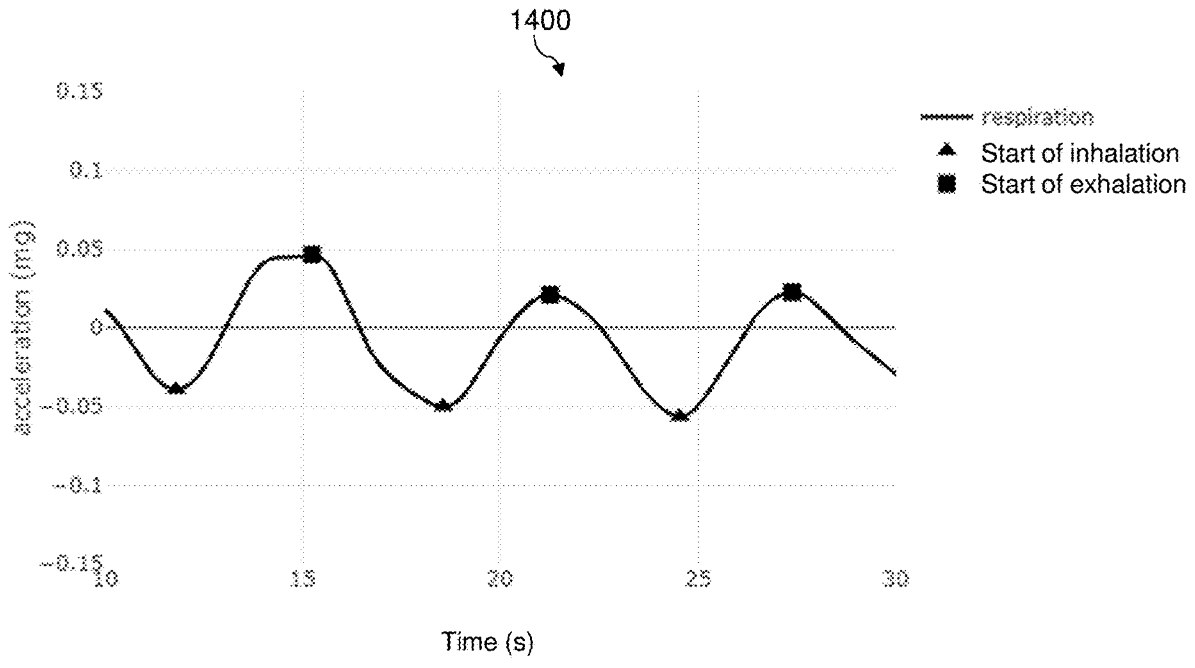
FIG. 13 represents, schematically, a signal of a step of determining a respiratory frequency of a method that is the subject of the invention.

The signals representative of a respiratory activity are shown in FIG. 12.

The step of determining a respiratory frequency comprises a step of detecting instants of inhalation and exhalation 610. For example, during the detection step 610, an inhalation instant corresponds to a local minimum and an exhalation instant corresponds to a local maximum.

The determination step also comprises a step of calculating a respiratory frequency 611. The frequency is calculated using the mean period between two inhalation and/or exhalation instants.

Figure 14:
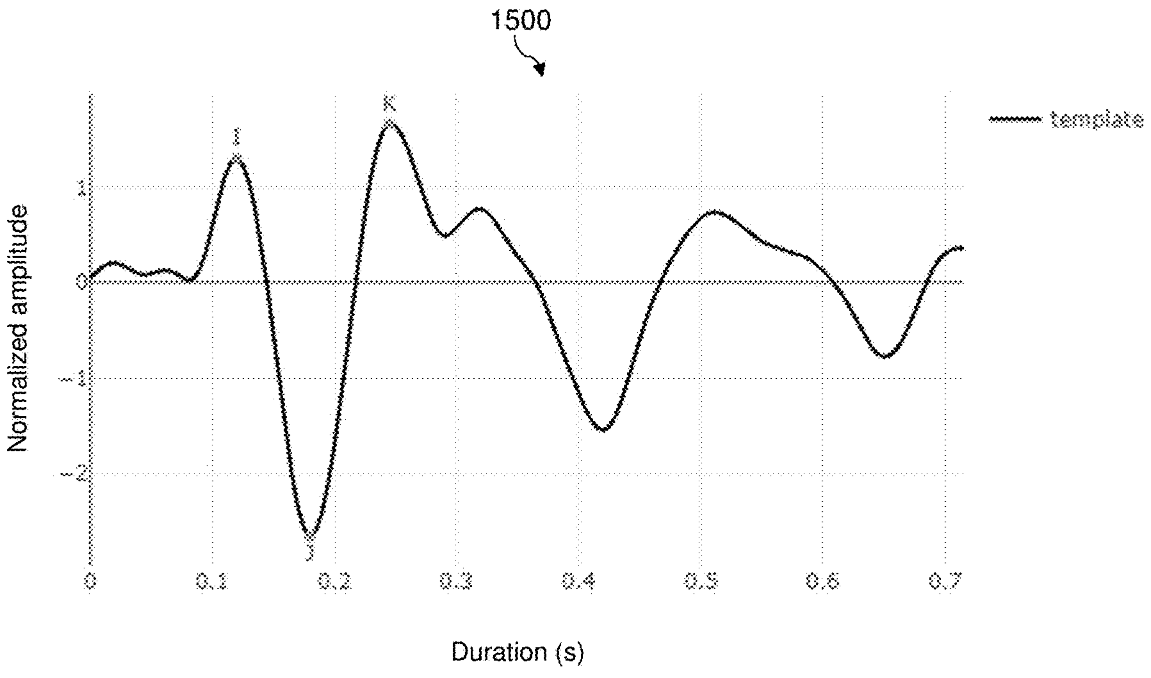
FIG. 14 represents, schematically, a model obtained by a method that is the subject of the invention.

The step of determining a heart rate comprises a step 612 of detecting an IJK complex by Dynamic Time Warping (acronym DTW). The IJK complex, FIG. 14, known in ballistocardiography, corresponds to the left ventricular systole. The IJ segment corresponds to the ventricular contraction and the JK segment corresponds to the ventricular relaxation. The J peak is taken as the reference for the heartbeat and for calculating the heart rate.

Then, for each segment, by performing a verification and a manual correction if necessary, the amplitude of the J peaks of the ballistocardiogram is automatically detected, and the minimum and maximum median values of the amplitude of the J peaks are determined. These statistical elements make it possible to account for the left ventricular ejection.

During the detection step 612, a model defined during the calibration phase is applied to the segments.

During the step 614 of calculating the heart rate, the mean heartbeat of the user is calculated using the applied model that minimizes the dynamic time warping. Once the model is applied, the J peaks of the IJK complexes are detected. The time period between two J peaks is calculated as the interval between each heartbeat. A linear interpolation is performed to sample the interval between two J peaks at 1 Hz. The inverse of this series is taken and multiplied by 60: the heart rate series in beats per minute (bpm) is obtained, sampled at 1 Hz after linear interpolation.

Preferably, the method 600 comprises a phase 700 of calibrating the model over a second predefined period, which comprises the following steps:

- capturing 701 a signal representative of a movement and/or variation of quasi-static stress produced by a user and traversing a support;
- segmenting, 703 to 712, the captured signal;
- detecting 714 an envelope and at least one period for each signal segment;
- calculating a center of each envelope in the period;
- superimposing 715 centers of each period; and
- for each segment of the signal, creating 718 a cardiac model corresponding to the mean of the superimposed points at each instant of the predefined period.

The capture step 701 of the calibration phase performs the capture step 601 of the method 600.

The steps of recording 702, detection 703 of an envelope, 707 and classification as a function of a movement, 708 of segmentation, 712 of classification as a function of a presence and 713 of filtering, corresponding respectively to steps 602 to 604, 606, 607 and 609 of method 600.

The hidden Markov model 605 used in the method 600 is obtained after initialization 704 and training 705 of a hidden Markov model using envelopes detected during the envelope detection step 703. The parameters of the trained hidden Markov model are then recorded 706 to be used in the method 600.

The presence model 608 used in the method 600 is obtained after initialization 709 and training 710 of the presence model using envelopes detected without movement after segmentation 708. The parameters of the trained presence model are then recorded 711 to be used in the method 600.

Figure 9:
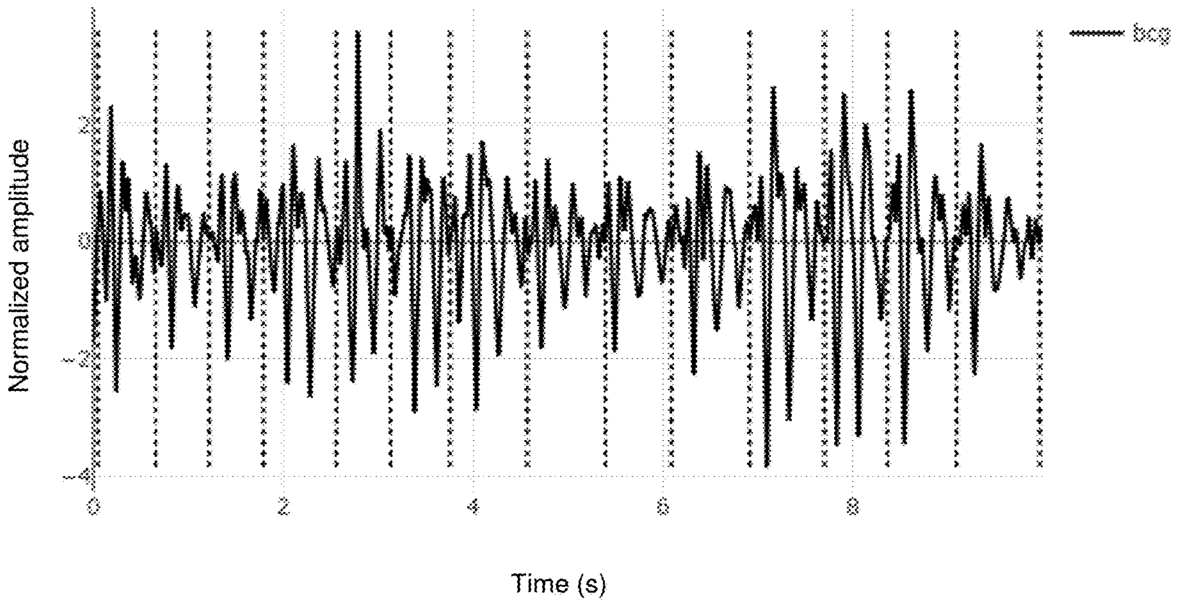
FIG. 9 represents, schematically, a signal of a step of obtaining a period of a method that is the subject of the invention.
Figure 10:
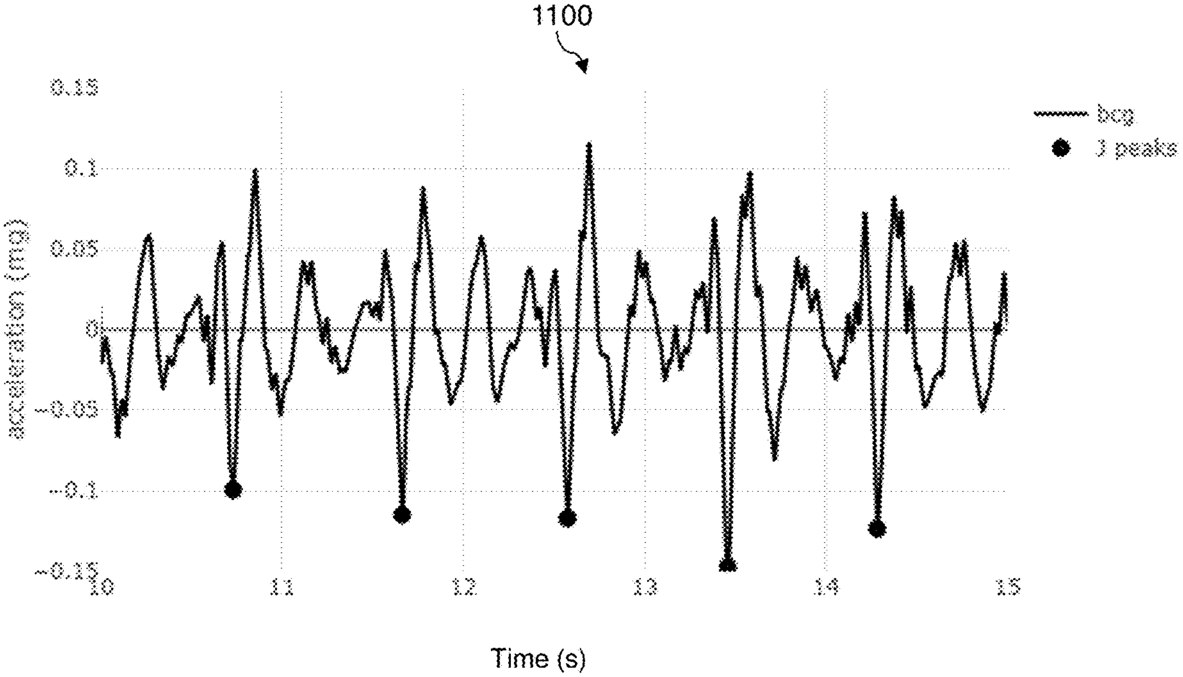
FIG. 10 represents, schematically, a signal of a step of determining a heart rate of a method that is the subject of the invention.

After the filtering step 713, the local minimums are determined for each envelope 714 of each segment, as shown in FIG. 10, which makes it possible to define the periods of the signal. The periods are shown by a dashed line in FIG. 9. The center of each period is defined by the position of the overall minimum of the cardiac signal in the period. Next, each period is superimposed 715 by positioning their centers on a shared reference, the center of the superimposition. The superimposition of the periods is shown in FIG. 11.

A model is then produced for each presence segment and stored 718 by calculating the mean of the points of the signals of these superimposed segments.

Dynamic time warping 716 (acronym DTW) of the model is performed with windows of the signal. A signal window has the mean duration of a heartbeat, comprising a contraction and a mechanical relaxation of the heart. As an example, the mean duration of a heartbeat is between 0.5 and 1 second in general.

Figure 11:
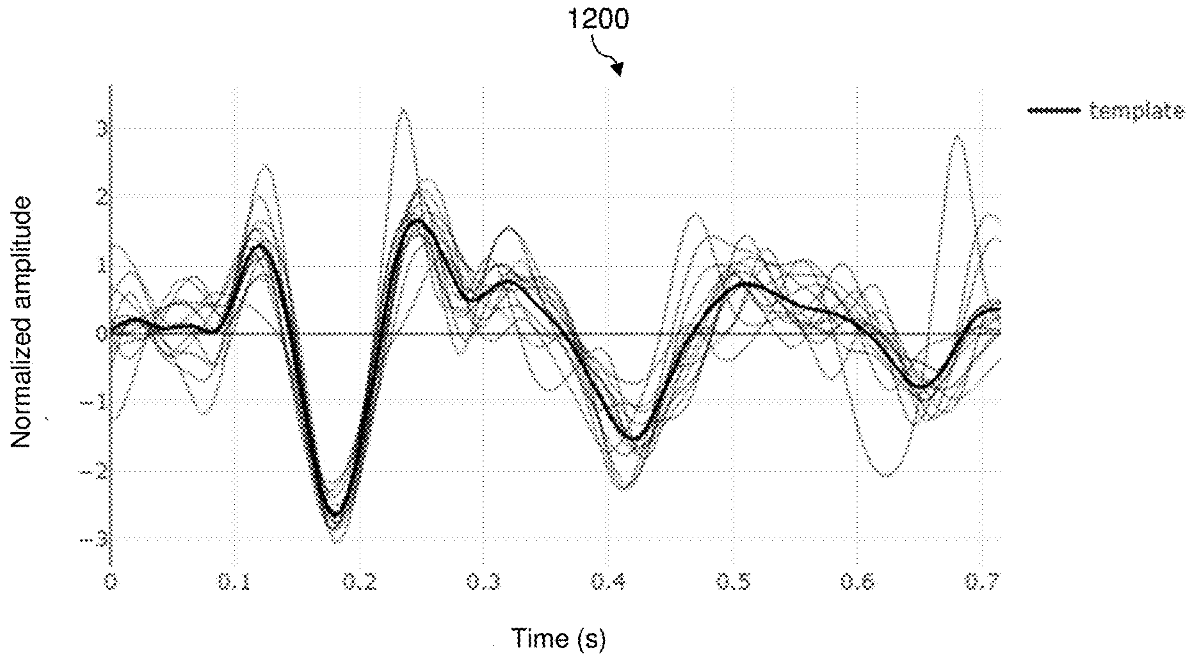
FIG. 11 shows, schematically, signals during a superimposition step of a method that is the subject of the invention.

For example, FIG. 11 shows ten signal windows which minimize the dynamic time warping distance with the model. FIG. 11 was constructed by choosing a window size, and the position of the J peak in this window. In the example shown in FIG. 11, the window size is 0.72 seconds and the position of the J peak in this window is 0.18 seconds. Then, for each local minimum of the signal, a window of the same size is selected so that the local minimum of the signal is positioned at 0.18 seconds from the start of the window. For each of these windows, the dynamic time warping distance is calculated and a threshold is applied to the dynamic time warping distances: the dynamic time warping distances less than the threshold correspond to heartbeats. The windows therefore closely resemble the model, they are heartbeats. The model, on which an IJK complex is referenced, is shown in isolation in FIG. 14.

The heartbeats are superimposed 715 to obtain a new model, representative of the recording studied. The new model is obtained by superimposing the ten heartbeats closest to the first model. The model is thus more specific than the initial model. A generic model has therefore been adapted to the recording of the user, the user's position and the support on which the user is resting.

For each presence segment, iterations of the detection 716 of the IJK complex, detection and superimposition of the periods 717 and 715 are performed until convergence of the heartbeat model.

In some embodiments, the device that is the subject of the invention comprises at least two stress and/or movement sensors placed according to different longitudes to correspond to two different sources. The term "longitude" refers to the dimension along an axis in the direction of the length. For example, one stress and/or movement sensor is placed facing the user's thorax, and one stress and/or movement sensor is placed facing the user's pelvis, feet or head.

In these embodiments, the method 600 comprises a step of measuring the arterial stiffness by measuring the Pulse Wave Velocity (acronym PWV). The step of measuring the arterial stiffness comprises a step of measuring the user's blood flow in at least two places where at least one sensor is positioned. The time periods between the J peaks of the ballistocardiogram corresponding to the user's thorax and the ballistocardiogram linked to the second location, for example the feet, are measured. Then the pulse wave velocity is calculated as a function of the time period measured and the distance between the sensors along the length.

EXAMPLES

Hereinafter, tests were performed with different guides and a benchmark comprising only one support. The term "upper surface" refers to the surface of the support on which a user lies.

In the following examples, each stress or deformation guide has a Young's modulus at least 10% higher than the value of the Young's modulus outside the stress or deformation guide.

Benchmark Support:

The benchmark support 105 is a 200×80 cm firm Malvik (registered trademark) mattress made of latex and polyurethane foam and a Utaker (registered trademark) pine bed, available at Ikea (registered trademark).

The base (X0,Y0,Z0) is orthonormal and fixed relative to the structure, for example the ground (see FIG. 2). When the individual is lying on his back:

- the axis X0 corresponds to the head to foot axis (the length of the mattress 105);
- the axis Y0 corresponds to the right to left axis (the width of the mattress 105); and
- the axis Z0 corresponds to the dorsal to ventral axis (direction of gravity) (the height of the mattress 105).

The mattress cover is removed. The sensor is attached directly onto the mattress with double-sided adhesive tape, centered on the following position, taking as reference center the top left corner of the upper surface of the mattress:

y0=−50 cm y0=−10 cm

These position coordinates of the sensor are retained subsequently, only the support and the fastening will change.

Example A

A three-dimensional textile layer from an Aerospacer (registered trademark) mattress topper by Medstrom (registered trademark) is added to the benchmark support 105. The three-dimensional textile layer is the deformation guide.

A three-dimensional textile layer has an anisotropic elastic modulus: the Young's modulus in the X0 direction is less than the Young's modulus in the Y0 direction.

The sensor is positioned on the upper surface of the three-dimensional textile layer at the same coordinates x0 and y0 as the benchmark measurement.

Example B

A tape made of cotton twill is added to the benchmark support 105. The cotton tape goes widthwise round the mattress, along the coordinate y=y0. The tape is held taut by a tightening loop made of polyamide.

The sensor is attached by a double-sided adhesive tape onto the upper surface of the tape, at x=x0. In this way, the sensor is positioned at the x0 and y0 coordinates on the upper surface of the tape.

Results

The amplitudes of the J peaks of the ballistocardiogram and the root-mean-square values of the ballistocardiogram and of the increased respiration, are compared for each support. Three consecutive tests are performed for each support, to make sure that the measurements are repeatable. The ambient noise is also indicated with a test with no person lying down.

Hereinafter, the term "performance levels" refers to the amplitude of the root-mean-square value of the ballistocardiogram captured, the minimum, maximum, median or mean amplitudes of the J peaks of the ballistocardiogram captured.

For the ballistocardiogram in the x direction, one measures that:

- the noise root-mean-square is of the order of eight µg;
- the signal-to-noise ratio varies between four and seven decibels according to configurations; and
- the guides of examples A and B increase the performance levels.

For the ballistocardiogram in the y direction, one measures that:

- the noise root-mean-square is of the order of nine rig;
- the signal-to-noise ratio varies between eight and ten decibels according to configurations; and
- the deformation guides of examples A and B increase the performance levels.

It is noted here that the root-mean-square value of the signal representative of acceleration is insufficient to characterize the performance levels of the guide that is the subject of the invention, and it is the amplitude of the J peaks that is most significant. In particular, the minimum amplitude of the J peaks for each recording is an interesting performance level, with the smallest J peak being the most difficult to detect since its amplitude is close to that of noise. For example, the guide of example A has a root-mean-square value of the signal representative of acceleration that is lower than the support with no guide, but the amplitudes of the J peaks are greater.

Even though they generally increase the performance levels, it is noted that the deformation guides can have several impacts on the performance levels, depending on the support used and according to the axes of movement considered. It can be seen that the guide of example B makes it possible to considerably improve the performance levels up to a 72% increase in the minimum amplitude of the J peaks. The guide of example A increases the performance levels on the x axis rather than on the y axis.

When the support is modified to bear a mattress with a cover, it can be seen that the guide of example B considerably increases the minimum amplitude of the J peaks, which can be up to twenty-five percent higher.

It is very important to distinguish the minimum and maximum amplitudes of the J peaks. In the same recording, the amplitude of the heartbeats, and of the J peaks in particular, varies with the respiration. The J peaks of low amplitude are the most difficult to detect. The most interesting performance level to evaluate is therefore the minimum amplitude of the J peaks.

The deformation guides of examples A and B make it possible to increase the minimum amplitude of the J peaks. For example, the guide of example A increases the minimum amplitude of the J peaks by two to thirty-five percent, and the guide of example B increases the minimum amplitude of the J peaks by twelve to seventy-two percent.

One can therefore see the benefits of the stress or deformation guides of the device that is the subject of the invention, and they have to be modeled mechanically and correctly sized to maximize the performance levels.

The contribution to the BCG of the nature of the bedding and of the deformation guide is examined below.

The deformation guides amplify the blood ejection force generated during systole and offer the possibility of developing a smartphone-based contactless method of monitoring for mechanical cardiac activity, including for newborn babies.

Digital signal processing algorithms have been developed to detect heartbeats, the heart rate, beat by beat, and the heart rate variability (HRV) in the signals of the BCG using methods in the time domain or time-frequency domain. The robustness to noise has also been examined and specific algorithms for heartbeat detection have been developed in the case of pediatric BCG, where the amplitude, compared to adults, can be about 30 times lower because of the small size and low cardiac contractile force. It is also shown that the resolutions of the smartphones' accelerometers are sufficient for them to be used for BCG monitoring in neonatology.

In a first experiment, the sensor is based on a Murata SCA100T-D02 (registered trademarks) two-dimensional analog accelerometer with an output noise density as low as 14 μg/sqrtHz. The sensor is incorporated in a housing made of ABS plastic and connected by a shielded cable to a Biopac MP36R (registered trademarks) acquisition unit for coupling, amplification and alternating current power. The analog output is alternating-current coupled, anti-alias filtered and amplified 100 times before being digitized at 1 kHz. In this configuration, the resolution is as low as $2^{21}$ LSB/g (least significant bit).

The process of capturing signals is repeated for several configurations of mattress (with or without cover) and for the following bedding: without deformation guide, adhesive tape made of polypropylene (PP), cotton tape, spacing tissues. Table 1 shows all these configurations. A control sample, with no person on the bed, is added to measure the noise baseline. Each configuration is repeated three times to eliminate the variability of the position of the bed.

In the second experiment, the positions of the bed and sensor are the same as in the previous experiment. This time, the sensor is based on a smartphone: it consists of an LSM6DSM 3D digital accelerometer from STMicroelectronics (registered trademarks), incorporated in a Motorola One (registered trademark) telephone. In this smartphone configuration, the sampling rate is 200 Hz, the resolution is $2^{12}$ LSB/g and the output noise density is 90 μg/sqrtHz. It is noted that these specifications are much lower than those of the sensor in the first experiment. The Fealing Android (registered trademark) application in background mode is used to record the samples of the accelerometer and export them to a computer.

The same adult lies on the bed, immobile and lying down for a sleep of 30 minutes, according to two different configurations: with the smartphone fixed by Velcro on bedding with a deformation guide, or directly on the mattress cover. Another sensor is used as a benchmark: the EMFIT QS (registered trademark) sensor of normal pressure, which provides a raw signal for sleep times longer than 20 minutes, in the breathing (0.07-3 Hz) and heart (1-35 Hz) frequency bands.

The first minute is eliminated for each recording, to ensure that the volunteer is relaxed and breathing slowly and regularly during the resulting one-minute recordings. The BCG's digital signals are filtered with third-order Butterworth filters, in particular a low-pass filter of 25 Hz and a high-pass filter of 2 Hz. These are applied before and after to avoid any phase distortion. Lastly, the signal is decimated to a sampling frequency of 200 Hz.

Figure 15:
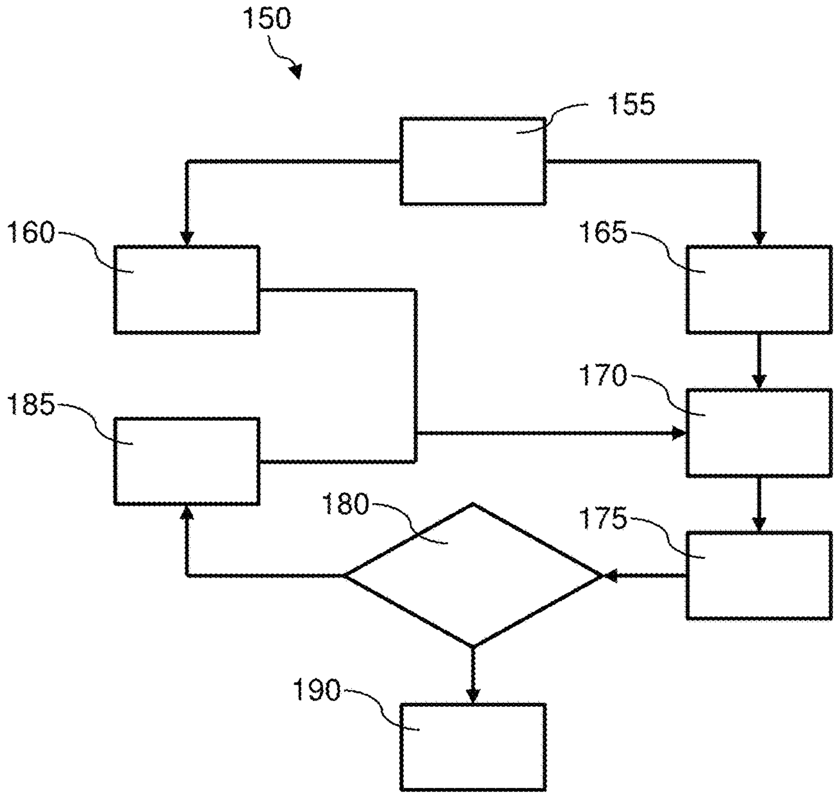
FIG. 15 represents steps of an algorithm for heartbeat detection.

The heartbeats are detected by means of a dynamic time warping (DTW) template matching algorithm, the steps of which are indicated in FIG. 15.

The J peaks of the BCG are defined as benchmark tags for the heartbeats.

FIG. 15 represents a pseudo-algorithm 150 for heartbeat detection using a DTW template matching method.

FIG. 15 shows a step 155 of segmenting the BCG with no movement; a step 160 of automatically detecting a heartbeat template or type; a step 165 of segmenting potential heartbeats, located round certain local extrema of the signal; a step 170 of measuring the DTW distance of the heartbeats from the template; a step 175 of detecting heartbeats, i.e. those with the smallest DTW distance; a step 185 of estimating the mean of the heartbeats selected, to refine the template for the new distance measurements with the candidates; and a step 180 of determining the convergence of the template. As long as convergence has not taken place, after the step 180, the cycle of steps 185, 170, 175 and 180 is continued. Once convergence is achieved, the detection of J peaks follows.

Figure 16:
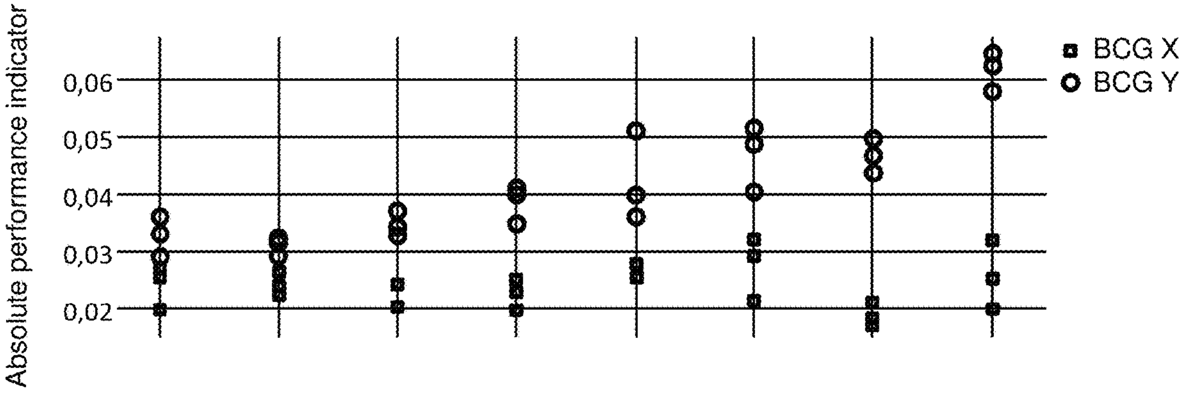
FIG. 16 represents performance indicators.

The median amplitude of the J peaks is a simple performance indicator, but does not take two phenomena into account:

- the modulation of the amplitude of the J peaks during the respiratory cycle, as shown in FIG. 16; and
- the non-linearity of the mechanical structure.

Consequently, the less detectable J peaks must be amplified in priority.

The first decile of the amplitude of the J peaks is selected for each BCG signal. The absolute performance indicator is the median value of these first deciles on the three recordings of this configuration.

The performance indicator is evaluated on each deformation axis, so as to be able to compare the influence of the deformation guide on each of these axes.

In the second experiment, the BCG signals with no movement are segmented and zeroed on average. The signal-to-noise ratio (SNR) of the signals recorded by each sensor is estimated and a transfer function is calculated, such as the relationship of the SNR of the sensors of smartphones to the SNR of the benchmark pressure sensor. This method is pertinent for the longest, noisiest segments, since it is not necessary to detect and verify heartbeats manually.

The gain is evaluated to the ratio between these transfer functions and can depend on the frequency, in particular on two frequency bands: the respiratory frequency band and the cardiac frequency band, previously defined as 0.07-3 Hz and 1-35 Hz. The frequency bands are filtered using third-order Butterworth filters.

The BCG signals during absence or presence are necessarily recorded at different time intervals. Ideally, the sensors of the smartphones record the BCG simultaneously; for reasons of simplicity, they are also recorded at different times. In total, two sleep sessions are recorded: one with a deformation guide and one without. For each of these sleep sessions, the BCG is segmented into segments with no movement, with or without presence, and with two different frequency bandwidths. The three axes of the accelerometer sensors are examined.

The conclusion of these experiments is that the configuration of the mattress has a direct impact on the performance indicator. In addition, the performance indicators are dependent on the axes. Three main results emerge from FIG. 16, which classifies configurations as a function of their performance indicators on the Y axis, with, from left to right, spacing tissues with cover, PP adhesive tape with cover, no guide with cover, no guide without cover, cotton tape with cover, spacing tissues without cover, PP adhesive tape without cover, cotton tape without cover.

Firstly, the Y axis transmits the BCG signal better than the X axis. This has been verified ($p<0.05$) for each configuration, except for {cover+3D tissue} where $p=0.053$, and {cover+cotton band} where $p=0.171$.

Secondly, the addition of a cover to the configuration of the mattress modifies the transmission of the BCG signal along the Y axis ($p<0.05$), except when no waveguide is used ($p=0.177$).

Thirdly, regardless of the configuration of the mattress, the deformation guide made of cotton tape improves the performance indicator along the Y axis, which is not the case for the other deformation guides. This has been verified for the Y axis with a mattress without cover ($p=0.001$), but not really with a mattress with cover ($p=0.230$).

Table 1 summarizes the performance indicators for the Y axis, which is the axis that gives the best results.

TABLE 1

Absolute/relative performance indicators on the Y axis.

| Deformation guide | Without deformation guide | | PP adhesive tape | | Cotton tape | | Spacing tissues | |
|---|---|---|---|---|---|---|---|---|
| No mattress cover | 0.040 | 0.0% | 0.047 | 17.6% | 0.063 | 57.4% | 0.049 | 23.0% |
| With mattress cover | 0.034 | 0.0% | 0.032 | −6.6% | 0.040 | 16.3% | 0.033 | −3.6% |

It can be seen that, in general, the cotton tape enables better transmission than the spacing tissues or PP adhesive tape.

The invention claimed is:

1. A ballistocardiography device comprising:

a non-homogeneous anisotropic support having a portion forming a stress or deformation guide and a portion transmitting fewer stresses or deformations in the frequency range between 0.05 Hz and 25 Hz; and at least one sensor of a signal representing at least one movement and/or variation of quasi-static stress of the guide in the frequency range between 0.05 Hz and 25 Hz, positioned facing the stress or deformation guide, wherein the stress or deformation guide is a surfacic element, and wherein the support has a generally parallelepipedal shape, whose largest dimension is called the “length”, smallest dimension is called the “thickness”, and intermediate dimension is called the “width”, wherein said at least one sensor is a sensor for capturing an inclination of the stress or deformation guide, and wherein said stress or deformation guide is positioned in a direction parallel to the width and passing through a source of stresses or deformations.

2. The ballistocardiography device according to claim 1, wherein the stress or deformation guide covers the support at least partially.

3. The ballistocardiography device according to claim 1, wherein the stress or deformation guide is tensioned along its length.

4. The ballistocardiography device according to claim 1, which comprises a means for tightening under tension the stress or deformation guide around the support.

5. The ballistocardiography device according to claim 4, wherein the means for tightening does not cover the entire width of the stress or deformation guide.

6. The ballistocardiography device according to claim 1, which comprises a means for fastening the stress or deformation guide to a rigid portion of the support.

7. The ballistocardiography device according to claim 1, which comprises a receptacle for a portable communicating terminal, such as a smartphone or a digital tablet.

8. The ballistocardiography device according to claim 1, wherein the stress or deformation guide has a Young’s modulus at least 10% higher than the value of the Young’s modulus outside the stress or deformation guide in at least one direction.

9. The ballistocardiography device according to claim 1, wherein the stress or deformation guide has a Young’s modulus with a progressive value.

10. The ballistocardiography device according to claim 1, wherein the guide for stresses or deformations comprises at least one woven material.

11. The ballistocardiography device according to claim 1, which also comprises a means for processing each signal captured by each sensor, and a means for comparing to at least one predefined model in order to deduce trends, troubles or anomalies from this.

12. A ballistocardiography method utilizing a device according to claim 1, comprising the following steps:

capturing a signal representative of a movement and/or variation of quasi-static stress produced by a user and traversing a support;

segmenting the captured signal;

filtering at least one segment of the captured signal providing a signal representative of a cardiac activity comprising at least two heartbeats;

applying a model to each period of the signal representative of a cardiac activity; and determining a heart rate and/or a heart rate variability.

13. The ballistocardiography method according to claim 12, which comprises a phase of calibrating the model, which comprises the following steps:

capturing a signal representative of a movement and/or variation of quasi-static stress produced by a user and traversing a support;

segmenting the captured signal;

detecting an envelope and at least one period for each signal segment;

calculating a center of each envelope in the period; superimposing centers of each period; and for each segment of the signal, creating a cardiac model corresponding to the mean of the superimposed points at each instant of the predefined period.

14. The ballistocardiography method according to claim 12, wherein the filtering step supplies a signal representative of a respiratory activity, the method also comprising a step of determining a respiratory frequency and/or apnea/dyspnea events as a function of at least one signal segment representative of a respiratory activity.

15. The ballistocardiography method according to claim 12, wherein the segmentation step comprises a step of removing each signal segment representative of a movement by the user and/or an absence of the user on the support.

16. The ballistocardiography device according to claim 1, wherein said surfacic element is defined as an element having thickness which is negligible with respect to length and width of the element.

* * * * *